United States Patent [19]

Gould et al.

[11] Patent Number: 5,025,476
[45] Date of Patent: Jun. 18, 1991

[54] REDOTOPOGRAPHY APPARATUS AND METHOD USING MOIRÉ FRINGE ANALYSIS TO MEASURE FOOT SHAPES

[75] Inventors: Nathaniel Gould, Boca Raton, Fla.; Michael Fontes, Hinesburg; Tyler R. Thessin, South Burlington, both of Vt.

[73] Assignee: Nathaniel Gould Diagnostics, Inc., Wallingford, Conn.

[21] Appl. No.: 264,908

[22] Filed: Oct. 31, 1988

[51] Int. Cl.[5] .............................................. G06K 9/00
[52] U.S. Cl. ........................................ 382/2; 382/4; 382/5; 33/3 B; 356/374
[58] Field of Search ........................... 382/2, 1, 4, 6, 5; 33/3 B, 3 C, 515; 356/374, 376, 383, 384

[56] References Cited

U.S. PATENT DOCUMENTS

| 2,009,340 | 7/1935 | Edwards | 356/376 |
|---|---|---|---|
| 3,627,427 | 12/1971 | Johnson et al. | 356/76 |
| 4,051,483 | 9/1977 | Suzuki | 346/33 A |
| 4,525,858 | 6/1985 | Cline et al. | 382/1 |
| 4,538,353 | 9/1985 | Gardner | 333/3 C |
| 4,541,113 | 9/1985 | Seufert et al. | 382/4 |
| 4,604,807 | 8/1986 | Bock et al. | 33/3 C |

FOREIGN PATENT DOCUMENTS 991996 1/1983 U.S.S.R. .
2052756A 1/1981 United Kingdom .

OTHER PUBLICATIONS

Gould, Nathaniel, M.D., Evaluation of Hyperpronation and Pes Planus in Adults, Clinical Orthopaedics and Related Research, vol. 181, pp. 37-45.
Drawing of pedotopography device used in clinical research.

Primary Examiner—Michael Razavi
Attorney, Agent, or Firm—DeLio & Associates

[57] ABSTRACT

A pedotopography apparatus which measures the shape of a foot by producing a moiré fringe pattern representative of the underside of the foot, capturing and storing an image of the moiré fringe pattern in an image storage buffer, analyzing the image to locate at least two points of interest on the foot and computing information corresponding to the distance between the two points. In the preferred embodiment the captured image is processed by Sobel convolution to enhance edges in the image. Both an apparatus and a method of processing are disclosed.

28 Claims, 3 Drawing Sheets

ABSOLUTE HORIZONTAL SOBEL

Fig. 4b.

THRESHOLDED ABSOLUTE HORIZONTAL SOBEL

Fig. 4c.

THRESHOLDED ABSOLUTE VERTICAL SOBEL

Fig. 4d.

THRESHOLDED NEGATIVE VERTICAL SOBEL

3×3 SOBEL KERNEL

REDOTOPOGRAPHY APPARATUS AND METHOD USING MOIRé FRINGE ANALYSIS TO MEASURE FOOT SHAPES

BACKGROUND OF THE INVENTION

1. Field of the Invention

This invention relates to devices for measuring the shape of a human foot. More particularly, this invention relates to devices which measure the shape of the foot by producing a moiré fringe pattern on the underside of the foot while the foot is bearing weight, and then analyze that pattern to determine the foot shape.

2. Description of Related Art

Previous devices for measuring the shape of a foot have generally employed one of two distinct methods of operation.

The first method involves mechanically measuring the shape of the foot by making physical contact between the sides of the foot and a probe. For example, the common foot-size measurement tool found in most shoe stores generally includes a pair of blocks, one of which is fixed and one of which slides along a distance scale between them. The heel of the foot is placed in contact with the fixed block and the sliding block is pushed into contact with the toes, after which the foot length can be read from the scale. Devices employing physical contact with the foot, however, often produce measurements which vary, even when measuring the same foot, due to the compressibility of the foot tissue and the difficulty of determining the exact moment of contact.

The second method involves placing the foot to be measured over an array of detectors sensitive to the presence or absence of light. The foot is then illuminated from above and an outline of the foot is determined by scanning the detectors An example of this type of device is found in U.S. Pat. No. 4,538,353 issued to Gardner and the related U.S. Pat. No. 4,604,807 issued to Gardner et al.

This method is an improvement over the first one in that it produces a complete foot outline, not just a single linear measurement of width or length. It also requires no physical contact with the sides of the foot which improves the repeatability of the measurements. However, it suffers from several inaccuracies of its own. The human foot does not have sides which are exactly square and perpendicular to its sole. Instead, they are curved and flare out from the portion of the sole in contact with the supporting surface. In the arch region, the sole of the foot may not be in contact with the supporting surface for a substantial distance inwards from the edge of the foot.

This three-dimensional nature of the foot permits light to leak under the edges of the foot activating the detectors and resulting in a detected foot outline which is much smaller than the actual foot. The extent of this undersizing varies depending on the foot being measured. One foot may make close contact with the supporting surface around its perimeter, or may have little or no arch thereby covering more detectors than another foot. Undersizing may also occur if the foot is not measured under load with the normal body weight applied.

This second method also suffers from problems with shadows cast by the foot and leg because of the difficulty of providing collimated illumination from directly above the foot.

Such prior art measuring devices have generally been used to measure the foot for shoe size and width. Many times, however, one wants to measure a foot in order to construct an orthotic insert for a shoe to balance the foot to a plantigrade position.

Such inserts have previously been prepared by taking an impression of the foot in a material that permanently deforms to follow the contours of the foot, thereby producing a mold. The insert is then produced either directly in that mold or on the exterior of a second mold produced by taking a positive casting from the first mold. However, small changes in the angle of insertion of the foot into the deformable media can result in an incorrect mold, and an incorrectly shaped insert. These problems are not present when the foot is measured with the pedotopography apparatus of the present invention.

Accordingly, one object of the present invention is to provide a pedotopography apparatus which is capable of measuring dimensions of the foot at an elevation above the plane of the supporting surface while the foot is under its normal standing load.

A second object of the invention is to provide a pedotopography apparatus which is capable of measuring the arch and other features of the foot within the perimeter of the foot.

Another object of the invention is to provide a pedotopography apparatus which can record images of the foot for subsequent review and analysis.

A further object of the invention is to provide a pedotopography apparatus which can produce a foot "signature" of measured dimensions of or locations on a foot and compare that signature to a database of previously measured feet to select an appropriately shaped shoe or insert.

SUMMARY OF THE INVENTION

The above, and other objects which will be apparent to those skilled in the art, are achieved in the present invention which provides a pedotopography apparatus comprising a means for producing a moiré fringe pattern representative of the topography of the underside of a foot to be analyzed. An image capture means is provided for capturing and storing an image of the moiré fringe pattern in an image storage buffer. The captured image is then provided to an image analyzing means which analyzes the image of the moiré fringe pattern to locate at least two points of interest on the foot. A computing means then calculates information, such as the length or width of the foot or the appropriate shoe size or insert, which corresponds to the distance between the two points.

In the preferred embodiment, the captured image is first processed by an image processing means which enhances edges in the captured image. The image processing may be performed by Sobel convolution or by other edge enhancement techniques.

The exact location of the points of interest may be more accurately determined by using the processed image to first identify their approximate positions and then examining the unprocessed image only in the vicinity of the approximately determined locations to find the exact location of the points.

In the most highly preferred design, the image processing means processes only a windowed portion of the captured image, the windowed portion being restricted principally to the portion of the image containing the foot thereby reducing processing time. In the analysis of two feet, a second windowed portion containing the image of the second foot may be mirror inverted left-for-right prior to processing so that the same processing routines may be used for both left and right subimages.

DETAILED DESCRIPTION OF THE INVENTION

Figures 1, 2, 3:
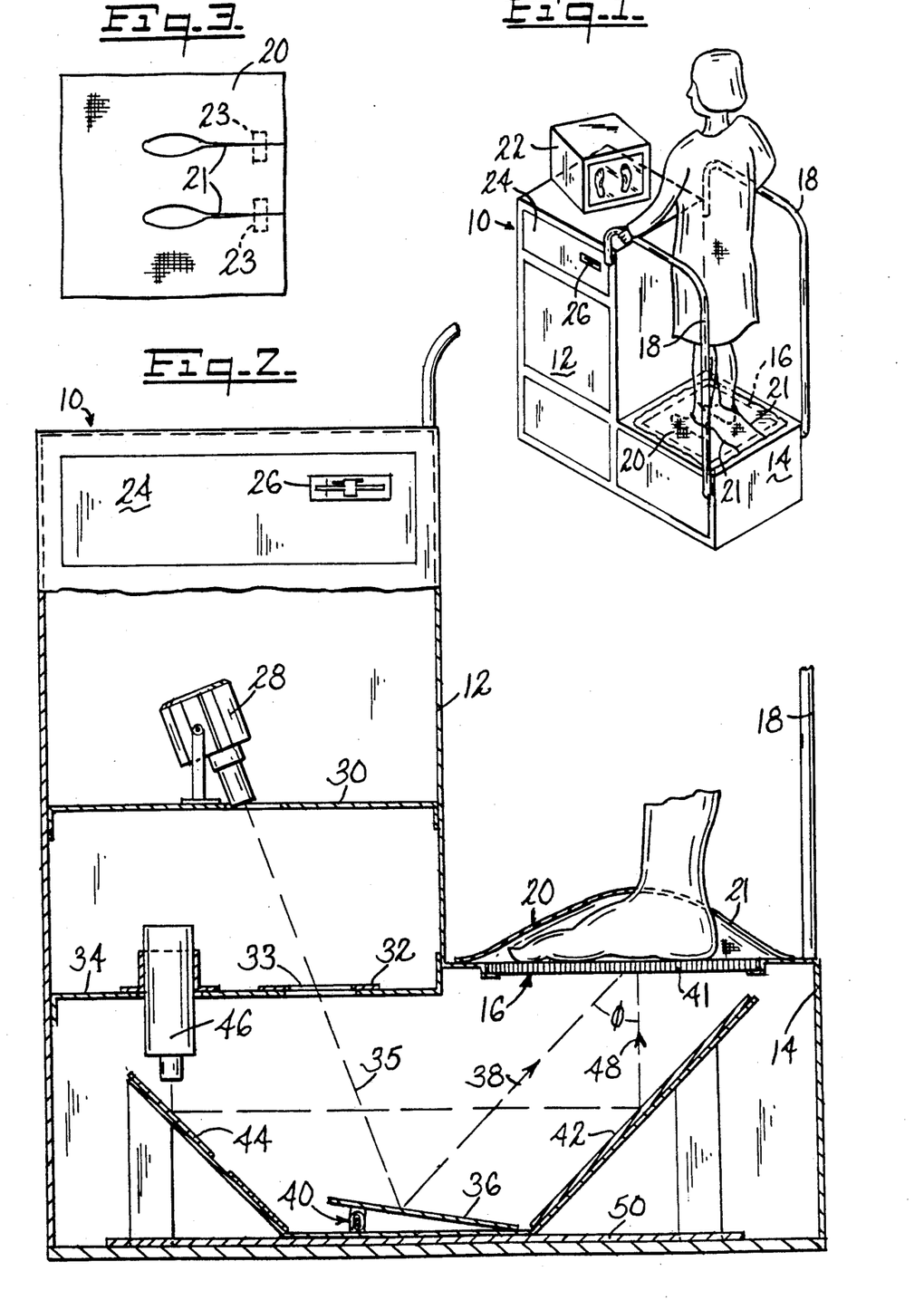
FIG. 1 is a perspective view of the pedotopography apparatus according to the present invention.
FIG. 2 is a side view in section of the invention showing the principle physical and optical elements of the invention.
FIG. 3 is a detailed view of the light shield used to prevent extraneous light from entering the invention.

A pedotopography apparatus according to the present invention is shown in perspective in FIG. 1, generally indicated by reference numeral 10.

The principal electrical and optical components are located in the main housing 12, a portion of which projects out to form a step 14. The upper surface of the step 14 is covered by a transparent support plate 16 (seen more clearly in FIG. 2) through which the underside of the foot can be viewed by the optical components within the main housing. On each side of the step portion a handrail 18 is provided permitting the patient whose feet are to be examined to stand comfortably upon the support plate.

An opaque light shield 20 (shown in detail in FIG. 3) fits around the patient's feet and prevents the patient's ankles and legs from being seen from below. The lightshield is designed to exclude extraneous light from entering the housing. It comprises an opaque fabric with two holes cut therein for the patient's legs. Slits 21 permit the shield 20 to be fitted around the patient's legs as seen in FIG. 1. Closures 23 may be formed from hook and loop fasteners to hold the shield in position.

A monitor 22 is positioned on the main housing for displaying the various images of the patient's feet. Beneath the monitor, within the upper portion of the main housing, a computer 24 is mounted with a conventional removable media disk drive 26 located therein.

As described in detail below, the computer must be sufficiently powerful to handle image processing tasks. The IBM AT computer or a similar machine employing the INTEL 80286 microprocessor performs well in this application, particularly when operated with clock speeds above 8 megahertz.

The removable media disk drive 26 is preferably capable of holding at least 1 megabyte of information. Data concerning the measurements on the patient's feet can then be stored on the disk, as well as images of the feet for the patient's records.

Referring now to FIG. 2, the major electrical and optical components can be seen. A light source 28 is adjustably mounted on the light source platform 30 and directs a beam of partially collimated illumination downwards through a light stop 32.

The light stop 32 includes a rectangular opening 33 therein which confines the light beam 35 to a rectangular shape and prevents extraneous light from passing below the camera platform 34.

The shaped light beam 35 then strikes the illumination mirror 36 and is reflected upwards towards the foot along a light path indicated by the arrow marked by reference numeral 38. The direction the light is travelling along this light path is referred to herein as the "first direction". The first direction 38 can be varied by moving the illumination mirror 36 on an adjustable mounting 40 which permits one end of the illumination mirror 36 to be raised and lowered thereby altering the angles of incidence and reflection.

The underside of the foot is uniformly illuminated by the shaped beam 38 which passes through the transparent support plate 16. The support plate 16 has a line grating 41 formed on its surface. The grating is generally indicated by the closely spaced vertical line hatching in FIG. 2 on the support plate 16. It should be understood, however, that the line grating 41 actually comprises a series of closely spaced fine parallel opaque lines which are on the surface of the support plate 16. The grating lines run across that surface in a direction which is perpendicular to the cross sectional plane of FIG. 2, i.e., from the right side of the patient in FIG. 1 to the left side, parallel to the front and rear edges of the support plate 16.

In the preferred embodiment, these opaque grating lines are ruled directly onto the surface of the support plate 16 which is formed of tempered glass sufficiently strong to easily support the weight of the patient. The ruled lines are preferably 0.7 mm center-to-center and 0.3 to 0.4 mm wide, however these dimensions may be varied provided that the line grating is capable of producing a moiré fringe pattern representative of the topography of the underside of the foot as described below.

Suitable gratings may also be produced by using a series of fine parallel wires suspended in a frame below the support plate 16 or through the use of a transparent film upon which opaque grating lines have been photographically reproduced.

The light beam 38, as it passes through the opaque grating lines, forms a series of shadow lines which are projected onto the underside of the foot. These shadow lines are straight wherever the foot is in contact with the support plate 16 or parallel to it and are curved along the contours of the foot wherever the surface of the foot lifts up from the support plate. The position of the shadow lines and their deviation from the straight carry information on the elevation of the foot above the support plate which can be obtained through the procedure described below.

After the light strikes the sole of the foot, it is reflected back through the grating 41 to the camera mirror 42 positioned directly beneath the foot, over to a second camera mirror 44 and up into the camera 46. In the preferred embodiment, the camera 46 is positioned pointing directly down into the second camera mirror 44 which is set at a 45° angle. Camera mirror 42 is also set at a 45° angle and thus the camera sees an image of the foot from the direction indicated by arrow 48 which is referred to herein as the "second direction". It will be noted that the second direction 48 is defined as being opposite to the direction light is travelling at this point.

Because the second direction 48 is substantially perpendicular to the plane of the support plate 16, the image seen by camera 46 has a uniform scale over the entire image area.

Although they are not shown, the support plate 16 also has several reference points, distance scales and window frame lines marked onto its surface which permits 1) calibration and alignment of the system, 2) calculation of the scale factor between distances (in pixels) on the camera image and distances on the surface of the support plate, and 3) accurate placement of the patient's feet on the plate. After assembly of the apparatus, the scale factor is carefully checked to ensure that it is substantially constant over the entire image area.

In the preferred embodiment, the light 28 is a 100 watt light source. At this relatively low wattage, the generated heat is kept to a minimum and a supplemental exhaust fan is not required provided that the main housing is properly ventilated.

The mirrors 36, 42 and 44 should all be of high quality, however, first-surface precision optical quality mirrors are not required and good plate glass mirrors may be used. The three mirrors 36, 42 and 44 are preferably mounted on a single tray 50 which can be removed for cleaning and adjustment of the mirrors.

As can be clearly seen in FIG. 2, the camera 46 views the foot through the grating 41 on the support plate 16. Thus, an undistorted image of the grating with straight grating lines is superimposed upon the image of the foot with the curved shadow lines. Because the first direction 38 is different from the second direction 48, the curved shadow lines carrying the elevation information about the foot interfere with the straight lines of the grating to produce a fringe pattern.

A fringe pattern of this type is known as a moiré fringe pattern. The fringes are formed along lines of constant elevation above the surface of the grating, with their spacing being determined by the grating size, the angle difference $\phi$ between the first direction 38 and the second direction 48 and the slope of the foot surface. Thus, the image seen by camera 46 has the appearance of a topographic map of the foot with the topographic fringe lines appearing wherever the foot is elevated above the surface of the support plate, which occurs principally at the arch and along the perimeter of the foot.

Figure 5:
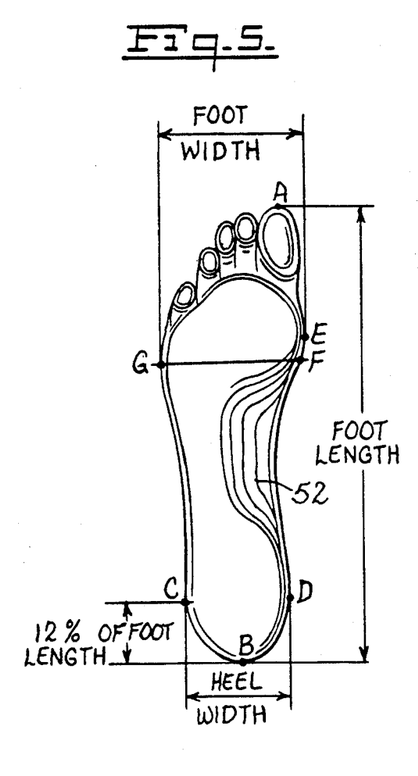
FIG. 5 shows several key points and measured dimensions on the foot.

FIG. 5 shows the image of a foot as it appears to the camera 46. At the edges of the foot, where the surface of the foot is nearly perpendicular to the support plate, the fringes 52 crowd closely together forming a dark band outlining the true outer perimeter of the foot. By locating the position of points of interest along this band, the outer dimensions of the foot can be accurately determined.

The image of the foot seen by the camera actually contains two sets of lines, namely the straight grating lines and the curved shadow lines cast by the light through the grating. The moiré fringes are an optical effect caused by the visual reinforcement which occurs wherever the two sets of lines cross. Nonetheless, the effect is such that the moiré fringes appear to be much broader, stronger and more widely spaced in the image than are the two sets of lines that form the fringes. When the image is viewed by the camera, the narrowly spaced grating lines are not fully resolved by the camera and are unnoticed in the image, and only the well-defined fringes can be clearly seen.

Although the specific means for producing the moiré fringe pattern described above is preferred due to its simplicity, other means are suitable. For example a projector may be used to project an image of the grating onto the foot from the first direction, and the camera may view the foot through another grating from the second direction. Alternatively, the second set of grating lines may be added electronically to the image seen by the camera.

Nevertheless, regardless of how the moiré fringe pattern is produced, an image of it is finally captured and stored in an image storage buffer. In the preferred embodiment, the camera 46 images the moiré fringe pattern onto an internal array of sensors producing a digitized image that is 512×512 pixels in size. Computer 24 contains an image capturing system connected to camera 46 which, upon activation of a remote switch, captures and stores the image seen by the camera.

The initial unprocessed image comprises a 512×512 array of pixels, each pixel having a gray-scale value from zero to 255. This resolution has been found to be sufficient for the moiré fringe analysis, however cameras with other resolutions have also been found to operate satisfactorily.

To summarize the operation of the pedotopography apparatus to this point, the patient steps up onto the support plate 16 facing the main housing 12 and grasps the hand rails 18. Light shield 20 is then placed around the patient's feet to prevent outside light from entering the camera system and interfering with the measurements.

The computer system is preferably designed to continuously display the camera picture on monitor 22 so that the patient may, under the operator's directions, move his or her feet into proper alignment with the reference points marked on the support plate's surface.

Once the patient's feet are in position, the operator activates a switch or presses a button on a keyboard (not shown) which signals the computer to capture the image displayed on the monitor. That captured image contains the topographically encoded height and shape information carried by the moiré fringes, which information may be determined by computerized analysis of the image as described below.

In most cases, it is not the magnitude of the height of the foot above the support plate which is the principal item of interest, but rather it is the projected location on the support plate of a point which is above the surface of the support plate which is of interest. For example, when determining the length of the foot, the tip of the longest toe will generally not be in contact with the support plate. The exact height of this point above the plate is generally not of interest, only its location over the plate needs to be known to calculate the length of the foot. As previously described, the moiré fringes delineate the maximum perimeter of the foot, including the point at the tip of the longest toe, the point at the heel, etc. Accordingly, by locating points on the perimeter fringe in the captured image and measuring the distance between them, any desired dimension, e.g., foot length, heel width, maximum foot width, etc., may be easily determined.

Whenever height information is needed, it is calculated by counting the number of fringes between the point of interest and a nearby point in contact with the supporting surface. As is well known to those familiar with moiré fringe topographic analysis, each new fringe occurs at a predetermined height above the previous fringe. That height difference is set by the relation:

$$h = \frac{d}{\tan \phi}$$

where h is the height difference, d is the spacing of the grating lines, and $\phi$ is the angle between the first (illumination) direction and the second (viewing) direction.

Thus, by counting the number of fringes, N, between a point in contact with the supporting surface and a point of interest, the height H of the point of interest can be determined by the relation:

$$H = Nh = \frac{Nd}{\tan \phi}$$

The disclosure below describes how each point of interest and the location of each fringe is found.

In the preferred design, after the image capture system is triggered, the computer automatically processes the image to identify points on the foot, determine distances between those points and produce an output of useful information which corresponds to those distances.

Two outputs which are commonly produced are foot length and foot width which may be displayed in units of length or in standard shoe size and width.

Preferably, additional points on the foot are measured which are related to the way in which the foot is shaped and how it bears the weight applied to it. By measuring a large number of feet, each of which is also carefully diagnosed by a trained physician, an information base can be accumulated. An unknown foot can then be measured and compared to this information base to produce an output quantizing the extent to which the foot deviates from the plantigrade status thereby assisting the physician in diagnosing and treating the foot.

Furthermore, the information base may contain a cross-reference to a standardized shoe insert or orthosis which has previously been found to balance a foot of similar measured structure to the plantigrade position.

Thus, another output of the measuring and analyzing process may be a code identifying a previously manufactured shoe or corrective insert which balances the foot to the neutral position. For unusual structural problems of the foot which do not correspond to previously measured and diagnosed feet in the database, the outputs may be the dimensions required to make a custom-made corrective shoe insert.

For each output, the starting point is to identify the location of points of interest on the foot. For example, FIG. 5 shows a patient's right foot, seen from below in the captured image. Two points of interest are points A and B corresponding to the tip of the toes and the bottom of the heel, respectively, which are used to determine the length of the foot. The perimeter fringes run through each point and the criterion of interest is the point on the fringe at the top of the image (for point A) and the point on the fringe at the bottom of the image (for point B).

Broadly speaking, the complete process involves 1) capturing the initial image 2) analyzing the image to locate the points of interest, and 3) computing output information which corresponds to the distance between the points.

Capturing and storing the image involves rapidly scanning the entire 512×512 pixel image array and storing an eight bit number corresponding to the light level for that pixel. Conventional image capture systems are widely available which provide this function. The complete captured image contains images of two feet as well as some border area and the reference points on the support plate. As described below, each of the pixels in the captured image is processed in the preferred embodiment. To increase processing speed, only that portion of the image containing the actual foot images needs to be stored. A windowed subimage of the entire image is typically stored for each foot which also reduces memory requirements in the computer 24 and storage space requirements.

The size and position of the required window may be calculated by the computer to frame each subimage of a foot wherever the foot appears in the complete image. However, it has been found to be simpler to mark the window on the surface of the support plate and have the operator ensure that the patient's feet are moved into the windows before the image is captured. Each foot subimage is typically about 100 pixels wide by 300–400 pixels high out of the full 512×512 image.

A second simplification in processing is to mirror invert the image of the left foot in a left-for-right inversion so that it appears to be the image of a right foot. This permits the same high speed image processing and analyzing routines to be used for both the left and right foot subimages.

Once the initial image is captured and the subimages extracted, they are passed individually to the image analyzer. In the preferred embodiment, this is a computer such as an IBM AT or compatible computer. Such computers, with interfaces for suitable image capturing systems, are widely available and are sufficiently fast and inexpensive enough for this application.

One method of operation of the image analyzer is the direct method. In this method, the image analyzer identifies point A at the tip of the toes by scanning each row of pixels in the foot subimage starting at the top and working down until the first row containing the foot perimeter moiré fringes is found. The pixels containing the fringes have a distinctly different intensity level than the background permitting them to be identified by comparing the intensity of each pixel to the average background intensity.

A similar method may be used to identify the row and column numbers for point B at the heel by searching rows from the bottom up. By searching in columns from the left and right, the position of points G and E may then be found setting the width of the foot. In fact, each point on the perimeter of the foot may be identified by tracing out, pixel by pixel, the perimeter fringes from the previously identified points on that perimeter.

Unfortunately, the direct method of locating the points described above, although feasible, requires a great deal of care to avoid false detection of the location of the fringes. Random noise in the image, internal reflections in the camera or optics, etc., all produce variations in intensity of points in the image which may be mistakenly detected as the moiré fringe at the perimeter.

Substantially improved results have been found by using image processing on the captured image to enhance edges in the image thereby increasing the contrast between the edges of the fringes and the background.

Although many different edge enhancement techniques are known, including Fast Fourier Transform filtering, Roberts convolutions, and others, the present invention has been found to operate most effectively using the Sobel convolution with a 3×3 video kernel to enhance vertical or horizontal edges, depending upon the point being located.

Figure 7:
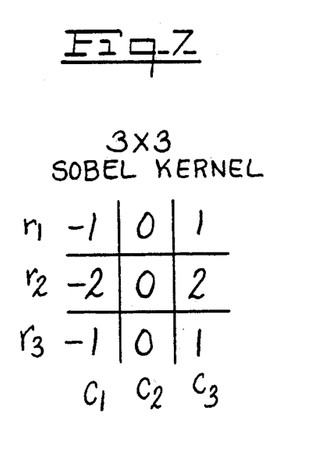
FIG. 7 shows a 3×3 Sobel kernel used in the Sobel convolution image processing.

FIG. 7 shows a 3×3 kernel to enhance vertical edges used in the image processing step which is also performed by computer 24. The 3×3 kernel contains nine elements found in three rows ($r_1$ to $r_2$) and three columns ($c_1$ to $c_3$) of numbers in a tic-tac-toe pattern. The vertical convolution video kernel of FIG. 7 is used in the following way to produce a processed image with enhanced vertical edges:

1. Select a pixel having an intensity magnitude p(x,y) in the original captured image, located at row=y, column=x.
2. Position the 3×3 video kernel over the selected pixel such that the central element in the kernel, $r_2$ $c_2$ is directly over the selected image pixel p(x,y) and the eight surrounding elements are over the eight pixels surrounding the selected pixel.
3. Multiply the numeric value in each element of the 3×3 kernel times the magnitude of the image pixel beneath that element.
4. Add the nine numbers obtained from the previous step to obtain a new intensity level p'(x,y) and insert that total as the intensity value at location (x,y) in a new processed image, i.e., the vertical sobel processed image.
5. Repeat the process for all of the original image pixels (x, y) to produce a complete processed image.

Specifically, the value of the pixel p'(x,y) in the processed image is:

$$p'(x,y) = r_1c_1\, p(x-1, y-1) + r_1c_2\, p(x, y-1) +$$
$$r_1c_3\, p(x+1, y-1) + r_2c_1\, p(x-1, y) + r_2c_2\, p(x,y) +$$
$$r_2c_3\, p(x+1, y) + r_3c_1\, p(x-1, y+1) + r_3c_2\, p(x, y+1) +$$
$$r_3c_3\, p(x+1, y+1)$$

or, substituting the actual elements of the vertical 3×3 kernel:

$$p'(x,y) = p(x+1, y-1) - p(x-1, y-1) +$$
$$2\, p(x+1, y) - 2\, p(x-1, y) + p(x+1, y+1) -$$
$$p(x-1, y+1)$$

Figure 6A:
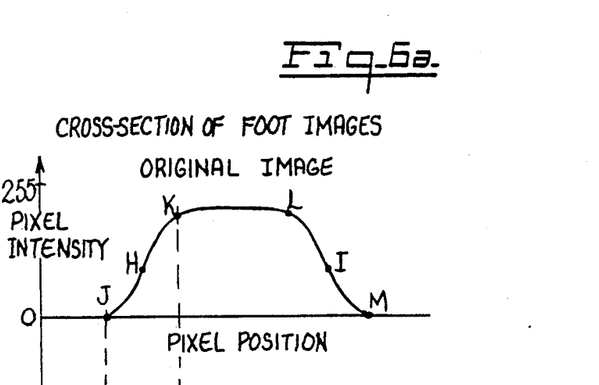
FIGS. 6a-6c are graphical representations of the results of the image processing.
Figure 6B:
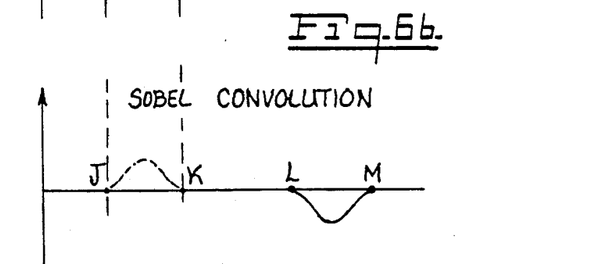
Figure 6C:
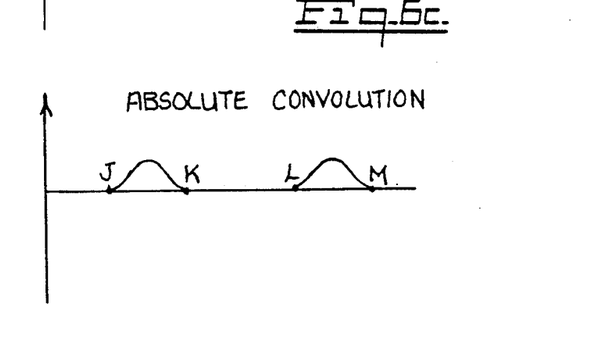

FIGS. 6a-6c show a two-dimensional simplified graphical representation of the results of this processing. FIG. 6a represents a slice through the unprocessed subimage of one foot along one row of pixels, for example from G to F in FIG. 5. The vertical scale shows the pixel intensity which ranges from 0 to 255. The horizontal scale shows the pixel position along G-F. Outside the foot the background intensity is at or near zero, and inside the interior of the foot, the intensity reaches a maximum. At the outer edge of the foot between points J and K, the pixel intensities gradually increase. An actual subimage would generally have substantially more fluctuations than the graph in FIG. 6a due to the fringes and other noise which have been ignored for this description of the Sobel processing.

Referring to FIG. 7 again, it will be seen that the elements in column one are equal to, but have the opposite sign as, the elements in column 3, while all the elements in column 3 are zero. Thus, wherever the unprocessed image has a uniform, unvarying intensity (which occurs in the center of the foot and in the background area), the Sobel convolution value will be zero. The positive contribution from pixels on the right side of the kernel will be exactly counteracted by the negative contribution from pixels on the left side of the kernel. This can be seen in FIG. 6b between points K-L and to the left of point J and the right of point M.

However, where the pixel intensity is varying, as between J-K and between L-M in FIG. 6a, the left and right side of the kernel contribute unequally to the result. Where the original image is increasing in intensity, as between points J and K in FIG. 6a, the positive contribution from the right side of the kernel outweighs the negative contribution, forming the positive "hump" between points J and K in FIG. 6b. Where the value is decreasing, as between points L and M, the negative contribution outweighs the positive, forming the negative dip between L-M in FIG. 6b.

FIG. 6c shows the absolute value of the convolution results of FIG. 6b which avoids the difficulty of displaying images with negative intensity values.

It can be seen in FIG. 6c that the absolute convolution enhances the position of the left and right edges in the image of FIG. 6a, clearly marking their positions. It is more difficult to see the manner in which random noise and fluctuations in the image are smoothed out, yet this happens also as a result of the 3×3 size of the video kernel, making it much easier to locate the edge positions at H and I.

While the foregoing has been described with respect to vertical Sobel convolutions, i.e., enhancement of vertical edges in the image, the same effect can be achieved for horizontal edges merely by rotating the 3×3 kernel of FIG. 7 by ninety degrees before use. If absolute convolutions are used, it does not matter in which direction the rotation is made.

FIG. 4 shows several actual edge enhanced processed images according to the present invention. FIG. 4a shows an absolute horizontal Sobel convolution. Intensity is simulated by the size of the dot printed at each pixel position. FIG. 4b is identical to FIG. 4a except that it has been "thresholded", i.e., all pixels having a processed intensity below a threshold value have been set to zero (shown as white). In both FIGS. 4a and 4b, it is easy to see that horizontal edges, for example, at the tips of the toes and the base of the heel have been emphasized, whereas vertical edges, for example along the edges of the feet, have almost disappeared from view.

Figure 4A:
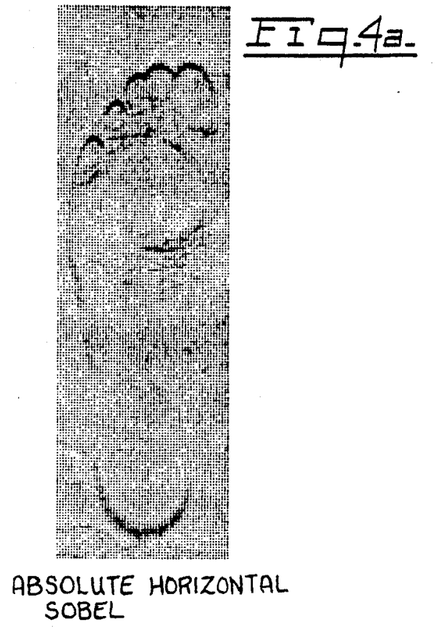
FIGS. 4a-4d show various states of the image processing of one foot.
Figure 4B:
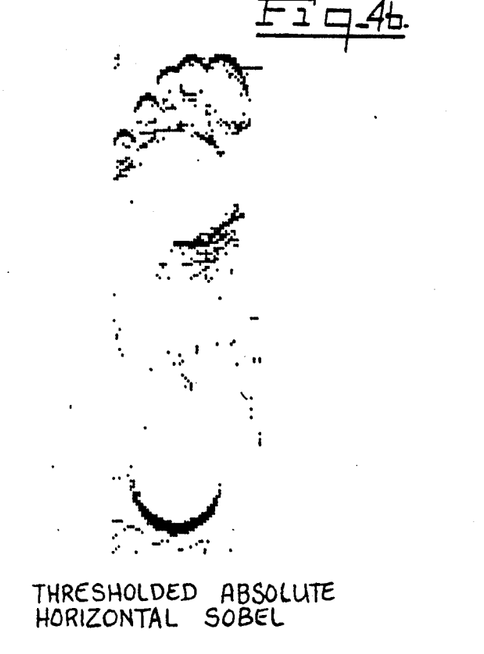
Figure 4C:
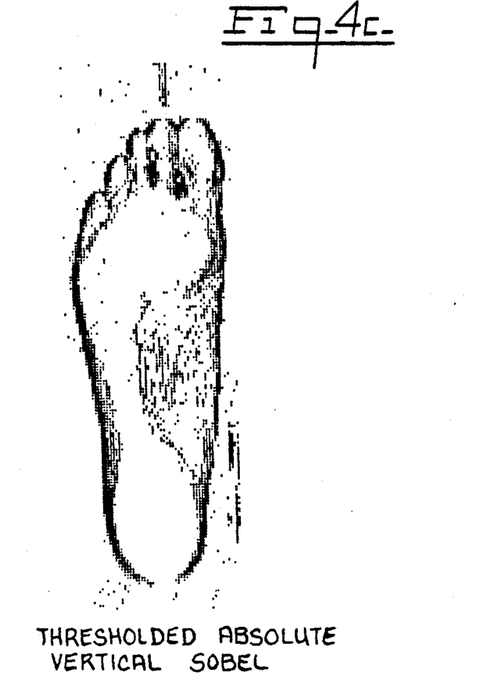

In contrast, FIG. 4c shows a thresholded absolute vertical Sobel convolution. In this image, the tips of the toes and the heels have almost disappeared while the vertical edges in the image of the feet are dark and enhanced.

Figure 4D:
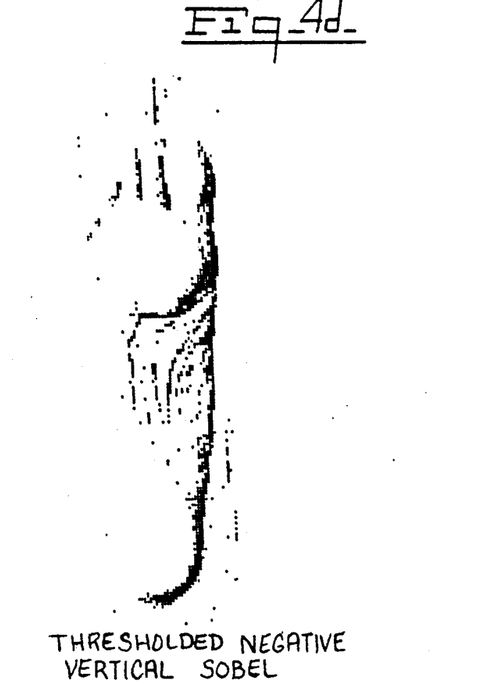

FIG. 4d shows a thresholded negative vertical Sobel, similar to an inverted FIG. 6b, wherein the absolute value of each image intensity has not been taken after the convolution, but a thresholding has been completed. The thresholding eliminates all of the negative value points and leaves only one edge visible along the medial or inner edge of the foot. This processing may be used to easily identify only points along this particular edge of the foot.

Although the 3×3 kernel shown in FIG. 7 is the preferred kernel, other values in the elements of the kernel may be employed, or the kernel may be expanded to 5×5, 7×7, etc., which provides further edge enhancement and smoothing, but substantially slows the speed of the image processing steps.

Continuing now with the description of operation, the captured image has been windowed and split into two subimages, one for each foot. One subimage is then inverted left for right to form two similar subimages which can be analyzed in the same manner and which have the medial side of the foot always on the right side of the image as seen in FIGS. 4 and 5.

In the most highly preferred embodiment, the subimages are then "clipped" before being processed with the Sobel convolution and thresholding operations. "Clipping" is similar to thresholding in that each image pixel is compared to a clipping value which, like the threshold value, is set above the average background level and below the average intensity level of the foot image area. However, in the clipping operation, the intensity of each pixel below the clipping level is increased to the clipping level instead of being reduced to zero as in the thresholding operation.

The clipping operation eliminates the majority of background noise fluctuations without introducing artificial edges or jumps in intensity level between points with intensities just below and points with intensities just above the clipping level.

Although any point of interest may be identified, generally the points identified are points A through G in FIG. 5. In order to identify point A, the image is first clipped and then processed as a thresholded absolute horizontal Sobel as shown in FIG. 4b. Each row of pixels in the processed subimage is then analyzed as described in the direct analysis procedure starting from the top and working down until the rows containing the enhanced edges are identified.

Although the processing smooths out many noise fluctuations in the raw image, this smoothing also has a tendency to smooth out the sharpness of the edges slightly making it somewhat more difficult to determine the exact edge location. As a result, in the processed image it is very easy to pick out the approximate location of the edge by setting a threshold level and finding all pixels in the searched row of pixels having a value above the threshold. The processing ensures that these pixels will be very close to the actual edge location and that a severe location error will not be made. However, due to the inherent smoothing which occurs during the processing, the actual edge location is more difficult to determine accurately. Accordingly, in the preferred embodiment of the invention, after the position of point A is approximately located in the processed image, the original unprocessed captured subimage is examined by the image processor only in the vicinity of the previously identified approximate location for point A to determine the accurate position of point A.

In a similar manner, the location of point B is identified by scanning rows in the processed image starting at the bottom and working upwards.

With the pixel coordinates of points A and B accurately located, the image analyzer provides this information to the calculating means which function is also preferably performed by computer 24.

The computing means can then calculate the length of the foot by determining the difference in row numbers between the row of pixels containing point A and the row of pixels containing point B. The scale factor previously determined for the image can then be employed to find the length of the foot in the desired units which may then be converted to shoe size.

In the manner described, each point of interest on the foot can be located and various dimension of the foot can be calculated. For the purpose of description of this invention, points A through G shown in FIG. 5 are located. The relative locations of these points form a "signature" for the foot which may be compared to a database of other stored foot signature patterns to determine the pattern which it most closely resembles.

Because the foot producing each foot signature in the database has been previously carefully analyzed and the results of that analysis have been indexed to each foot signature, the computing means may be used to select the analysis for the matching foot signature. Provided that the signature points are carefully selected, the resulting output will provide an accurate indication of foot shape.

Points A-G have been found to form a suitable signature for selecting shoe size and width, the length of a corrective insert for a shoe and its width at the heel and in the area beneath the ball of the foot. Other points may be added to refine the signature for accurate diagnosis of problems with the foot structure such as pes planus (flat foot), hyperpronation, etc.

To form the signature of points A-G, points A and B are first located in the manner described and the length of the foot is calculated. The width of the heel between points C and D is then determined by examining the thresholded absolute vertical Sobel processed image of FIG. 4c.

Points C and D are preferably located by selecting a row of pixels to be analyzed which are a selected percentage of the length of the foot up from the heel point B. In the described embodiment, this selected percentage is 12% of the length of the foot which has been empirically found to give a good indication of heel width for the signature. The row of pixels at the 12% point is then scanned, first in the processed image to identify the approximate location for C and D, then in the unprocessed image to determine final accurate position.

Point E is located at the head of the first metatarsal. When the foot is properly positioned on the support plate, point E will be the point on the perimeter of the foot which is farthest to the right as seen in FIG. 5. This point can be identified in the same manner as points A and B by scanning from the right instead of the top or bottom.

Point F is located approximately 2 mm below point E. This point has also been empirically determined and provides a good point at which the width of the foot can be measured. Next, the image analyzer analyzes the row of pixels along the line F-G to determine foot width.

As can be seen from the above description, the computer 24 preferably serves all the functions of processing the image to enhance the edges, analyzing the image to locate the points of interest, and computing the system output.

The computed output is then displayed on the monitor or it may be printed on a printer or other output device. The unprocessed image and the output information are also written onto a disk in the disk drive 26 for storage in the patient's records.

It will thus be seen that the objects set forth above, among those made apparent from the preceeding description, are efficiently obtained and, since certain changes may be made in the construction set forth above without departing from the spirit and scope of the invention, it is intended that all matter contained in the above description as shown in the accompanying drawings shall be interpreted as illustrative and not in a limiting sense.

What is claimed is:

1. A pedotopography apparatus comprising:
   means for producing a moiré fringe pattern representative of the topography of the underside of a foot to be analyzed;
   said fringe pattern being formed between the line grading and the line grating shadow on the underside of the foot;
   image capture means for capturing and storing an image of the moiré fringe pattern in an image storage buffer;
   image processing means for enhancing edges in the captured image;
   image analyzing means operatively connected to the image capture means for analyzing the image of the moiré fringe pattern to locate at least two points of interest on the foot; and
   computing means for calculating information corresponding to the distance between the two points.

2. A pedotopography apparatus according to claim 1 wherein the image processing means performs the edge enhancement by Sobel convolution.

3. A pedotopography apparatus according to claim 2 wherein the Sobel convolution is performed with a video kernel of 3×3 pixels.

4. A pedotopography apparatus according to claim 1 wherein the image processing means preferentially enhances edges which are substantially perpendicular to the centerline of the foot.

5. A pedotopography apparatus according to claim 4 wherein one of the at least two points identified by the image processing means is located at the back of the heel, the other is located at the tip of the forwardmost toe, and the distance between them is calculated by the computing means to determine the length of the foot.

6. A pedotopography apparatus according to claim 1 wherein the image processing means preferentially enhances edges which are substantially parallel to the centerline of the foot.

7. A pedotopography apparatus according to claim 6 wherein one of the at least two points identified by the image analyzing means is located at an inner edge of the foot, the other is located at the outer edge of the foot, and the distance between them is calculated to determine a width of the foot at a selected position.

8. A pedotopography apparatus according to claim 7 wherein the selected position at which the width of the foot is first determined is selected by the computing means which first calculates the length of the foot and then calculates the selected position by taking a predetermined percentage of the calculated length of the foot.

9. A pedotopography apparatus according to claim 8 wherein the width of the foot at the heel is determined by the identifying inner and outer edge points for the foot at approximately twelve percent (12%) of the length of the foot.

10. A pedotopography apparatus according to claim 7 wherein the selected position at which the width of the foot is determined is selected by the computing means after the image analyzing means identifies a specified point of interest on the foot, said selected position being calculated as a predetermined distance away from the specified point of interest.

11. A pedotopography apparatus according to claim 10 wherein the specified point of interest is located at the base of the first metatarsal.

12. A pedotopography apparatus according to claim 11 wherein the width of the foot is determined approximately two millimeters from the head of the first metatarsal in the direction of the heel of the foot.

13. A pedotopography apparatus according to claim 1 wherein the image analyzing means first analyzes the output of the image processing means containing the enhanced edges to determine approximate positions for the two points and then analyzes the non-edge enhanced image in the vicinity of the approximate positions to determine final accurate positions for the two points.

14. A pedotopography apparatus according to claim 1 wherein the means for producing the moiré fringe pattern representative of the underside of the foot comprises:
   a transparent support plate suitable for supporting the weight of a person standing with at least one foot thereon;
   the line grating;
   a light source positioned to illuminate the foot from a first direction through the line grating to form the line grating shadow on the underside of the foot;
   a camera positioned to view the foot through the line grating from a second direction.

15. A pedotopography apparatus according to claim 14 wherein the camera is positioned such that the second direction from which the camera views the foot is substantially perpendicular to the plane of the support plate.

16. A pedotopography apparatus according to claim 14 wherein the illumination from the light arrives at the foot traveling in the first direction after reflection from an illumination mirror.

17. A pedotopography apparatus according to claim 16 wherein the illumination mirror is adjustable to vary the first direction.

18. A pedotopography apparatus according to claim 14 further including at least one camera mirror in which the camera views the foot from the second direction.

19. A pedotopography apparatus according to claim 18 further including two camera mirrors, one of said camera mirrors being positioned beneath the support plate.

20. A pedotopography apparatus according to claim 19 wherein the camera mirrors are mounted in a removable tray.

21. A pedotopography apparatus according to claim 14 further including an opaque light shield covering the support plate and the upper surface of the foot and having an opening therein through which the leg of the person projects whereby extraneous light is prevented from entering the camera.

22. A pedotopography apparatus according to claim 21 wherein the opening in the light shield is fitted below the ankle of the person to prevent an image of the ankle or the leg from being seen by the camera.

23. A pedotopography apparatus according to claim 1 further including output means for providing the calculated information to an operator of the pedotopography apparatus.

24. A pedotopography apparatus comprising:
   a line grating;
   a light source positioned to illuminate the underside of a foot from a first direction through the line grating to form a line grading shadow on the underside of the foot;

a camera positioned to view the underside of the foot from a second direction;

image capture means for capturing and storing a first image of the foot from the camera;

image processing means for processing the first image with an edge-enhancement algorithm to produce a second image;

image analysis means which analyzes the second image of the foot to approximately identify the location of at least two points on the foot and then analyzes the first image, in the vicinity of the approximate positions to identify accurate positions for the two points; and computing means for calculating information corresponding to the distance between the two points.

25. A pedotopography apparatus according to claim 24 wherein the first image contains images of a pair of feet, and the image processing means processes a first windowed portion of the first image, the windowed portion being restricted principally to the portion of the first image containing the image of only one foot.

26. A pedotopography apparatus according to claim 25 wherein the image processing means processes a second windowed portion of the first image, said second windowed portion being restricted principally to the portion of the first image containing the image of the other foot, said second windowed portion being inverted left for right prior to processing.

27. A method for measuring the shape of a foot comprising:

(a) producing a moiré fringe pattern representative of the topography of the underside of a foot to be analyzed between the line grating and the shadow of the line grating;

(b) capturing and storing a first image of the moiré fringe pattern;

(c) processing the first image to enhance edges thereby forming a second image;

(d) analyzing the second image to locate at least two points of interest on the foot; and (e) computing information corresponding to the distance between the two points of interest.

28. A method for measuring the shape of a foot according to claim 27 further including the step of analyzing the first image in the vicinity of at least one of the two points located on the second image to obtain a more accurate location for the at least one point.

* * * * *